US011655210B2

(12) United States Patent
Fava et al.

(10) Patent No.: US 11,655,210 B2
(45) Date of Patent: May 23, 2023

(54) COMPOUND FOR IMPROVING L-ARGININE BIOAVAILABILITY

(71) Applicant: The General Hospital Corporation, Boston, MA (US)

(72) Inventors: Maurizio Fava, Newton, MA (US); Xudong Huang, Andover, MA (US)

(73) Assignee: The General Hospital Corporation, Boston, MA (US)

( * ) Notice: Subject to any disclaimer, the term of this patent is extended or adjusted under 35 U.S.C. 154(b) by 226 days.

(21) Appl. No.: 17/056,521

(22) PCT Filed: May 20, 2019

(86) PCT No.: PCT/US2019/033064
§ 371 (c)(1),
(2) Date: Nov. 18, 2020

(87) PCT Pub. No.: WO2019/222726
PCT Pub. Date: Nov. 21, 2019

(65) Prior Publication Data
US 2021/0206717 A1 Jul. 8, 2021

Related U.S. Application Data

(60) Provisional application No. 62/673,328, filed on May 18, 2018.

(51) Int. Cl.
C07C 279/12 (2006.01)
(52) U.S. Cl.
CPC .................. C07C 279/12 (2013.01)
(58) Field of Classification Search
CPC ................................... C07C 279/12
See application file for complete search history.

(56) References Cited

U.S. PATENT DOCUMENTS

| 8,952,045 B1 | 2/2015 | Kramer et al. |
| 2008/0213883 A1 | 9/2008 | Davis et al. |
| 2010/0196939 A1 | 8/2010 | Morris et al. |
| 2017/0071883 A1 | 3/2017 | Alevizache et al. |
| 2017/0096449 A1 | 4/2017 | Mathias et al. |

FOREIGN PATENT DOCUMENTS

WO WO 2016/054259 4/2016

OTHER PUBLICATIONS

Maes et al. Acta Psychiatr Scand 1998: 97: 302-308 (Year: 1998).*
Klotz et al. Urol Int. 1999;63(4):220-3. (Year: 1999).*
Tousoulis et al. Vascular Medicine 2002; 7: 203-211 (Year: 2002).*
Yi et al. Int J Clin Exp Pathol (2009) 3, 211-238 (Year: 2009).*
Ma et al. Current Pharmaceutical Design, 2010, 16, 392-410 (Year: 2010).*
Valayannopoulos et al. JMID vol. 35, Issue1 Jan. 2012 pp. 151-157 (Year: 2012).*
Ali-Sisto et al., "Global arginine bioavailability ratio is decreased in patients with major depressive disorder," J. Affect. Disord., 2018, 229:145-151.
Appleton, "Arginine: Clinical potential of a semi-essential amino acid," Altern. Med. Rev., 2002, 7:512-522.
Barassi et al., "Levels of L-arginine and L-citrulline in patients with erectile dysfunction of different etiology," Andrology, 2017, 5(2):256-261.
Cao et al., "L-Arginine supplementation inhibits the growth of breast cancer by enhancing innate and adaptive immune responses mediated by suppression of MDSCs in vivo," BMC: Cancer, 2016, 16:343, 11 pages.
Castillo et al., "Splanchnic metabolism of dietary arginine in relation to nitric oxide synthesis in normal adult man," Proc. Natl. Acad. Sci. USA, 1993, 90:193-7.
Chaubourt et al., "Nitric oxide and l-arginine cause an accumulation of utrophin at the sarcolemma: a possible compensation for dystrophin loss in Duchenne muscular dystrophy," Neurobiol. Dis., 1999, 6:499-507.
Chilosi et al., "Neuropsychological profile and clinical effects of arginine treatment in children with creatine transport deficiency," Orphanet. J. Rare Dis., 2012, 7:43, 9 pages.
Deveaux et al., "L-Arginine Supplementation Alleviates Postprandial Endothelial Dysfunction When Baseline Fasting Plasma Arginine Concentration Is Low: A Randomized Controlled Trial in Healthy Overweight Adults with Cardiometabolic Risk Factors," J. Nutr., 2016, 146:1330-1340.
Dong et al., "Effect of oral L-arginine supplementation on blood pressure: A meta-analysis of randomized, double-blind, placebo-controlled trials," Am, Heart J., 2011, 162:959-965.
Esnafoglu et al., "Decreased plasma agmatine levels in autistic subjects," J. Neural. Transm., 2018, 125(4):735-740.
Freitas et al., "Agmatine, a potential novel therapeutic strategy for depression," Eur. Neuropsychopharmacol., 2016, 26(12):1885-1899.
Hafner et al., "Improved Muscle Function in Duchenne Muscular Dystrophy through L-Arginine and Metformin: An Investigator-Initiated, OpenLabel, Single-Center, Proof-Of-Concept-Study," PLoS One, 2016, 11(1):e0147634, 19 pages.
International Preliminary Report on Patentability in International Appln. No. PCT/US2019/033064, dated Dec. 3, 2020, 7 pages.
International Search Report and Written Opinion in International Appln. No. PCT/US2019/033064, dated Jul. 17, 2019, 9 pages.
Jezova et al., "High trait anxiety in healthy subjects is associated with low neuroendocrine activity during psychosocial stress," Prog. Neuropsychopharmacol. Biol. Psychiatry, 2004, 28:1331-1336.

(Continued)

Primary Examiner — Jeffrey S Lundgren
Assistant Examiner — William Y Lee
(74) Attorney, Agent, or Firm — Fish & Richardson P.C.

(57) ABSTRACT

The present application relates to a compound which may be useful for mediating NO production and improving L-arginine bioavailability in a subject. Pharmaceutical compositions comprising the compound and methods of using the compound are also provided.

6 Claims, 4 Drawing Sheets

(56) References Cited

OTHER PUBLICATIONS

McRae, "Therapeutic Benefits of l-Arginine: An Umbrella Review of Meta-analyses," J. Chiropr. Med., 2016, 15(3):184-189.

Nader et al., "Effect of agmatine on experimental vascular endothelial dysfunction," Hum. Exp. Toxicol., 2016, 35(5):573-82.

Neis et al., "Therapeutic potential of agmatine for CNS disorders," Neurochemistry International, 2017, 108:318-331, Accepted Manuscript.

Popolo et al., "L-Arginine and its metabolites in kidney and cardiovascular disease," Amino Acids, 2014, 46:2271-2286.

Rhim et al., "The Potential Role of Arginine Supplements on Erectile Dysfunction: A Systemic Review and Meta-Analysis," J. Sex Med., 2019, 16(2):223-234.

Smriga et al., "Oral treatment with L-lysine and L-arginine reduces anxiety and basal cortisol levels in healthy humans," Biomed. Res., 2007, 28:85-90.

Tangphao et al., "Pharmacokinetics of intravenous and oral L-arginine in normal volunteers," Br. J. Clin. Pharmacol., 1999, 47:261-266.

Yi et al., "L-Arginine and Alzheimer's Disease," Int. J. Clin Exp. Pathol., 2009, 2:211-238.

International Search Report and Written Opinion in International Appln. No. PCT/US2020/060441, dated Feb. 10, 2021, 10 pages.

\* cited by examiner

COMPOUND FOR IMPROVING L-ARGININE BIOAVAILABILITY

CROSS-REFERENCE TO RELATED APPLICATIONS

This application claims the benefit of U.S. Provisional Application Ser. No. 62/673,328, filed May 18, 2018, the disclosure of which is incorporated herein by reference in its entirety.

FEDERALLY SPONSORED RESEARCH OR DEVELOPMENT

This invention was made with Government support under Grant No. R01AG056614, awarded by the National Institutes of Health. The Government has certain rights in the invention.

TECHNICAL FIELD

The present application relates to a compound which may be useful for mediating NO production and improving L-arginine bioavailability in a subject.

BACKGROUND

L-arginine is one of the essential amino acids for human health, and nitric oxide (NO) is an important cellular signaling molecule involved in many physiological and pathophysiological processes. L-arginine is a substrate for different forms of NO synthase (NOS) that catalyze NO production in the L-arginine-to-NO metabolic pathway. It has been used as a natural supplement for boosting NO production.

SUMMARY

The present application provides, inter alia, a compound which is:

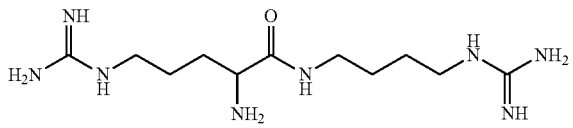

or a pharmaceutically acceptable salt thereof.
In some embodiments, the compound is:

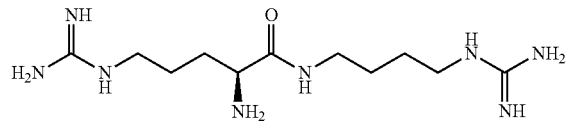 [SMILES: N=C(N)NCCCCNC(=O)[C@@H](N)CCCNC(=N)N]

or a pharmaceutically acceptable salt thereof.

The present application further provides a pharmaceutical composition comprising the compound a compound provided herein (e.g., 2-amino-5-guanidino-N-(4-guanidinobutyl)pentanamide), or a pharmaceutically acceptable salt thereof, and a pharmaceutically acceptable carrier.

The present application further provides a method of increasing the global arginine bioavailability ratio (GABR) in a subject, comprising administering to the subject an effective amount of a compound provided herein, or a pharmaceutically acceptable salt thereof.

The present application further provides a method of treating or preventing a disease or disorder in a subject, comprising administering to the subject an effective amount of the compound provided herein, or a pharmaceutically acceptable salt thereof.

In some embodiments, the disease or disorder is associated with abnormal levels of L-arginine, abnormal levels of agmatine, or a combination thereof, in the subject, compared to a normal subject.

In some embodiments, the disease or disorder is selected from a neurological disorder, a psychiatric disorder, a neurodegenerative disease, a cardiovascular disease, a renal disease, a urological or sexual disorder, cancer, and a genetic disorder.

In some embodiments, the disease or disorder is a neurological disorder. In some embodiments, the treating comprises reducing brain oxidative stress in the subject, reducing neuroinflammation in the subject, reducing proapoptotic signaling in the subject, mediating NO production in the subject, or any combination thereof. In some embodiments, the treating comprises mediating NO production in the subject. In some embodiments, the mediating is inhibiting.

In some embodiments, the psychiatric disorder is major depressive disorder (MDD) or an anxiety disorder.

In some embodiments, the disease or disorder is a cardiovascular or renal disease. In some embodiments, the cardiovascular or renal disease comprises hypertension.

In some embodiments, the treating comprises improving postprandial endothelial dysfunction in the subject.

In some embodiments, the disease or disorder is a urological or sexual disorder. In some embodiments, the urological or sexual disorder is erectile dysfunction.

In some embodiments, the disease or disorder is a neurodegenerative disease. In some embodiments, the neurodegenerative disease is Alzheimer's disease.

In some embodiments, the disease or disorder is cancer. In some embodiments, the treating comprises slowing tumor growth, inhibiting tumor metastases, improving immune function, or any combination thereof. In some embodiments, the cancer is selected from the group consisting of breast cancer, sarcoma, and lung cancer.

In some embodiments, the disease or disorder is a genetic disorder. In some embodiments, the genetic disorder is Duchenne Muscular Dystrophy (DMD) or autism spectrum disorder. In some embodiments, the genetic disorder is Duchenne Muscular Dystrophy (DMD). In some embodiments, the genetic disorder is autism spectrum disorder.

In some embodiments, the method provided herein is a method of treating the disease or disorder in the subject. In some embodiments, the method provided herein is a method of preventing the disease or disorder in the subject.

In some embodiments, the compound is administered as an adjunctive therapy in combination with one or more additional therapeutic agents, compared to a normal subject.

In some embodiments, the disease or disorder is associated with abnormal levels of L-arginine in the subject, compared to a normal subject. In some embodiments, the disease or disorder is associated with abnormal levels of agmatine in the subject, compared to a normal subject. In some embodiments, the disease or disorder is associated with abnormal levels of L-arginine and abnormal levels of agmatine in the subject, compared to a normal subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Figure 1:
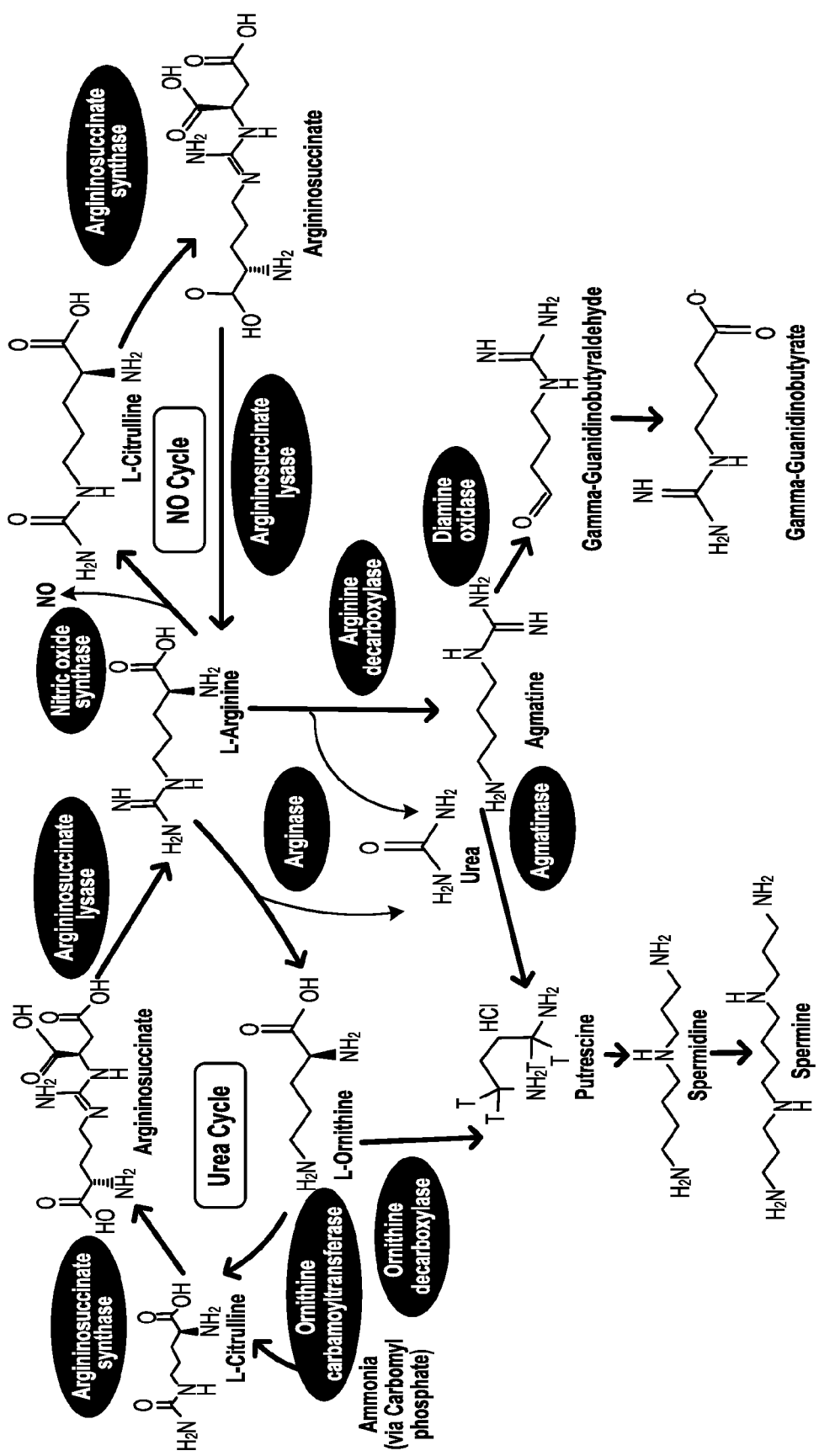
FIG. 1. shows a representative schematic of the L-arginine/NO/agmatine pathway.

Reduced L-arginine bioavailability has been implicated in many human diseases—hypertension-related cardiovascular and renal diseases (see e.g., Popolo et al., *Amino Acids.* 2014, 46:2271-2286; Ji et al., *Am. Heart J.* 2011, 162:959-965; Deveaux et al., *J Nutr.* 2016; 146:1330-1340), metabolic syndrome X, urological or sexual disorders such as Erectile Dysfunction (ED) (see e.g., Appleton, *Altern. Med. Rev.* 2002, 7:512-522; Barassi et al, *Andrology,* 2017, 5(2): 256-261; Chang Rhim et al, *J. Sex Med.* 2019, 16(2):223-234), neurodegenerative diseases such as Alzheimer's disease (AD) (see e.g., Yi et al., *Int. J. Cin. Exp. Pathol.* 2009, 2:211-238), psychiatric disorders such as depression (e.g., major depressive disorder; see e.g., Ali-Sisto et al, *J. Affect. Disord.* 2018, 229:145-151, schizophrenia, and the like (see e.g., Ali-Sisto et al., *J. Affective Disorders,* 2018, 229; 145-151), anxiety disorders (see e.g., Smriga et al, *Biomed. Res.* 2007, 28:85-90; Jezova et al, *Prog. Neuropsychopharmacol Biol. Psychiatry* 2004, 28:1331-1336), Duchenne Muscular Dystrophy (DMD) (see e.g., Chaubourt et al., *Neurobiol. Dis.* 1999, 6:499-507; Hafner et al, *PLoS One,* 2016, 11(1):e0147634); cerebral creatine (Cr) deficiency which results in mental retardation, speech and language delay, autistic-like behavior and epilepsy (CRTR-D) (see e.g., *Orphanet. J. Rare Dis.* 2012, 7:43), and improving postprandial endothelial dysfunction (see e.g., Deveaux et al, *The Journal of Nutrition,* 2016, 146(7):1330-1340; Nader et al., *Hum. Exp. Toxicol.* 2016, 35(5):573-82). In addition, L-arginine supplementation enhances both innate and adaptive immunity and slows down cancer cell growth (see e.g., Cao et al, *BMC Cancer,* 2016, 16:343). It has been shown that L-arginine may improve immune function of cancer patients when administered in high doses, as it has several immunomodulatory effects such as stimulating T- and natural killer cell activity and influencing pro-inflammatory cytokine levels. Without being bound by theory, it is believed that the compound of the present application may perform the same function as L-arginine at lower doses.

Oral supplementation with L-arginine has been administered to subjects in doses ranging from 1-20 g/day for a variety of clinical indications, including hypertension, hypercholesterolemia, coronary artery disease, congestive heart failure, peripheral arterial disease, sexual dysfunction, major depressive disorder, sickle cell disease, and in elderly humans, in attempts to improve NO-mediated vascular function (see e.g., McRae, *J. Chiropr. Med.* 2016, 15(3): 184-189). Metabolic data from experimental and human studies suggest that after oral administration, L-arginine is extensively metabolized by arginase in the gut wall and liver (see e.g., Castillo et al, *Proc. Natl. Acad. Sci. USA* 1993, 90:193-7). This may limit its bioavailability as a substrate for NOS and subsequent effect on vascular function.

The in vivo pharmacokinetics of L-arginine are suboptimal due to fast pre-systemic elimination by the intestinal and liver arginase activity (see e.g., Tangphao et al., *Br. J. Clin. Pharmacol.* 1999, 47:261-266). As such, even at large oral doses (e.g., gram quantities), at risk of inducing side effects, its bioavailability is still very modest and treatment is less cost-effective. For example, the absolute bioavailability of a single oral 10 g dose of L-arginine is about 20%, with the baseline plasma concentration of L-arginine on a normal diet over 8 hours being about 15.1±2.6 µg/mL (~86.7 µM±14.9 µM), with peak concentration at 50.0 µg/mL±13.4 µg/mL (~287.0 µM±76.9 µM), occurring 1 h after administration. Although therapeutic agents that mitigate the above medical conditions are available, having more effective drugs or even nutraceuticals with fewer side effects and higher bioavailability is still an unmet medical need.

A metabolite from L-arginine metabolic pathway, agmatine (see e.g., FIG. 1), has been proposed as a neuroprotectant for treating brain disorders by suppressing oxidative stress, neuroinflammation, pro-apoptotic signaling, and NO production (see e.g., Neis et al., *Neurochemistry International,* 2017, 108:318-331) and to serve as a treatment for major depressive disorder (see e.g., Freitas et al *Eur. Neuropsychopharmacol.* 2016, 26(12):1885-1899). In addition, decreased agmatine levels have been shown in autism (see e.g., Esnafoglu E, & İrende İ. *J. Neural. Transm.* (Vienna). 2018, 125(4):735-740).

Accordingly, the present application provides a compound synthesized from conjugating L-arginine with agmatine (i.e., a conjugate of L-arginine and agmatine), that is believed to decompose in vivo into L-arginine and agmatine by peptidase. Without being bound by theory, the compound provided herein (see Example 1) is expected to be attacked by arginase more slowly than L-arginine, and agmatine can preserve physiological stores of L-arginine by mediating NO production. As such, even at a lower dose, the compound of the present application will increase bioavailability of L-arginine, and consequential efficacy, by slowing down pre-systemic elimination by arginase as it is not an immediate substrate for the enzyme. The compound of the present application is not expected to exhibit toxicity and/or immunogenecity in view of the chemical structure and predictable major break-down products, L-arginine and agmatine, due to peptidase action in vivo.

Compounds & Synthesis

The present application provides a compound, which is:

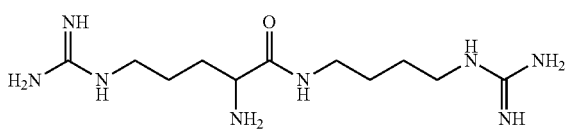 [SMILES: N=C(N)NCCCCNC(=O)C(N)CCCNC(=N)N]

(i.e., 2-amino-5-guanidino-N-(4-guanidinobutyl)pentanamide), or a pharmaceutically acceptable salt thereof.

In some embodiments, the compound is a pharmaceutically acceptable salt of:

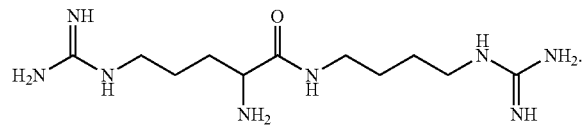 [SMILES: N=C(N)NCCCCNC(=O)C(N)CCCNC(=N)N]

In some embodiments, the compound is a hydrochloric acid salt of

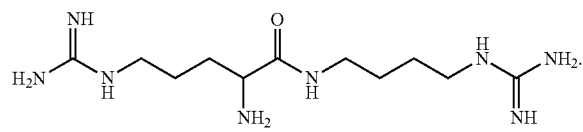 [SMILES: N=C(N)NCCCCNC(=O)C(N)CCCNC(=N)N]

In some embodiments, the compound is the free base form of:

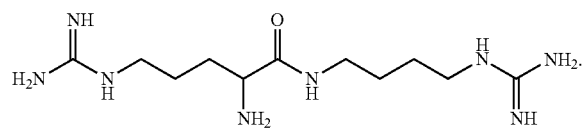 [SMILES: N=C(N)NCCCCNC(=O)C(N)CCCNC(=N)N]

In some embodiments, the compound is:

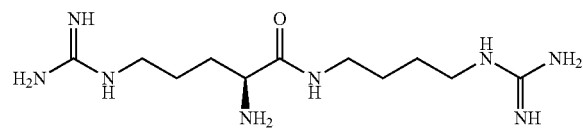 [SMILES: N=C(N)NCCCCNC(=O)[C@@H](N)CCCNC(=N)N]

or a pharmaceutically acceptable salt thereof.

In some embodiments, the compound is a pharmaceutically acceptable salt of:

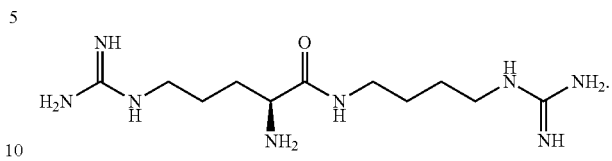

In some embodiments, the compound is a hydrochloric acid salt of

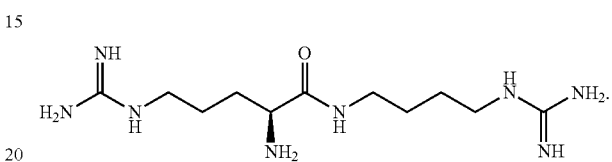

In some embodiments, the compound is the free base form of:

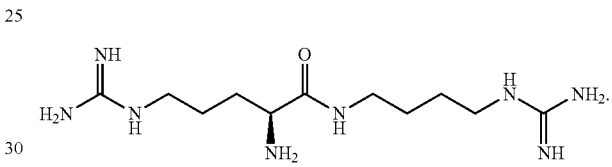

As will be appreciated, the compound provided herein (i.e., 2-amino-5-guanidino-N-(4-guanidinobutyl)pentanamide, or a pharmaceutically acceptable salt or specific isomer thereof) can be prepared using known organic synthesis techniques and can be synthesized according to any of numerous possible synthetic routes.

For example, 2-amino-5-guanidino-N-(4-guanidinobutyl) pentanamide may be prepared according to the procedure shown in Scheme I.

Scheme I.

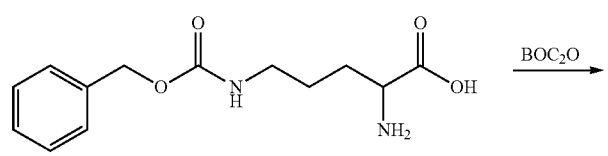

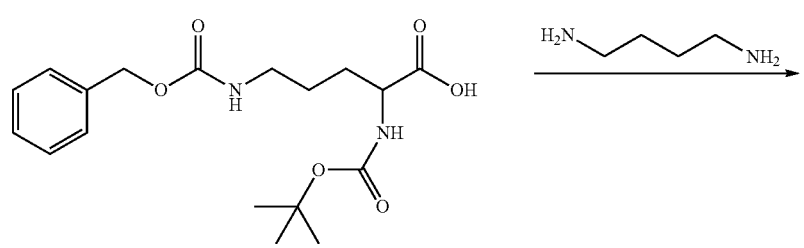

Compound A

-continued

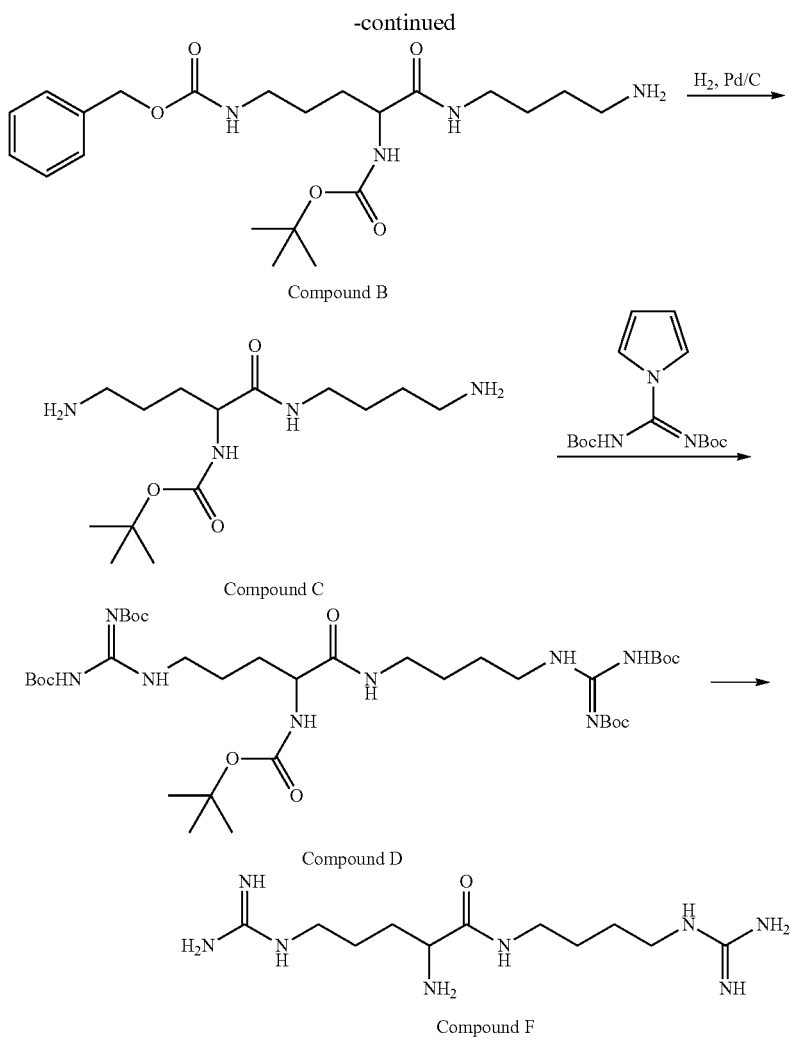

It will be appreciated by one skilled in the art that the syntheses described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LC/MS), or thin layer chromatography (TLC). The compounds can be purified by those skilled in the art by a variety of methods, including high performance liquid chromatography (HPLC) and normal phase silica chromatography.

The term "compound" or "conjugate" as used herein is meant to include all stereoisomers, geometric isomers, tautomers, and isotopes of the structures depicted. Compounds or conjugates herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system. Tautomeric forms can be in equilibrium or sterically locked into one form by appropriate substitution.

All compounds, and pharmaceutically acceptable salts thereof, can be found together with other substances such as water and solvents (e.g., hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

As used herein, the expression, "room temperature", is understood in the art and refer generally to a temperature, e.g. a reaction temperature, that is about the temperature of the room in which the reaction is carried out, for example, a temperature from about 20° C. to about 30° C.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmacetical Science,* 66, 2 (1977). Conventional methods for preparing salt forms are described, for example, in *Handbook of Pharmaceutical Salts: Properties, Selection, and Use,* Wiley-VCH, 2002.

Unless specifically defined, compounds provided herein can include all isotopes of atoms occurring in the intermediates or final compounds. Isotopes include those atoms having the same atomic number but different mass numbers. Unless otherwise stated, when an atom is designated as an isotope or radioisotope (e.g., deuterium, [$^{11}$C], or [$^{18}$F]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium). Synthetic methods for incorporating radioisotopes into organic compounds are well known in the art, and one of ordinary skill in the art will readily recognize methods applicable for the compounds provided herein.

Methods of Use

The present application further provides methods of treating a disease in a subject in need thereof. As used herein, the term "subject," refers to any animal, including mammals. Exemplary subjects include, but are not limited to, mice, rats, other rodents, guinea pigs, rabbits, dogs, cats, swine, cattle, sheep, horses, primates, and humans. In some embodiments, the subject is a human.

In some embodiments, the present application provides a method of increasing the global arginine bioavailability ratio (GABR) in a subject, comprising administering to the subject an effective amount of the compound provided herein, or a pharmaceutically acceptable salt thereof. In vivo GABR can be calculated, for example, according to Equation 1 (units based on concentration of each component in the equation):

$$GABR=\text{L-arginine}/(\text{L-ornitine}+\text{L-citrulline}) \qquad \text{Equation 1.}$$

In some embodiments, the present application provides a method of treating or preventing a disease or disorder in a subject, comprising administering to the subject an effective amount (e.g., a therapeutically effective amount) of the compound provided herein, or a pharmaceutically acceptable salt thereof.

In some embodiments, the disease or disorder is associated with abnormal levels of L-arginine, abnormal levels of agmatine, or a combination thereof, in the subject, compared to a normal subject.

In some embodiments, the disease or disorder is associated with abnormal levels of L-arginine in the subject, compared to a normal subject. In some embodiments, the disease or disorder is associated with abnormally low levels of L-arginine in the subject, compared to a normal subject.

In some embodiments, the disease or disorder is associated with abnormal levels of agmatine in the subject, compared to a normal subject. In some embodiments, the disease or disorder is associated with abnormally low levels of agmatine in the subject, compared to a normal subject.

In some embodiments, the disease or disorder is associated with abnormal levels of L-arginine and agmatine in the subject, compared to a normal subject. In some embodiments, the disease or disorder is associated with abnormally low levels of L-arginine and agmatine in the subject, compared to a normal subject.

In some embodiments, the disease or disorder is selected from a psychiatric disorder, a neurological disorder, a neurodegenerative disease, a cardiovascular disease, a renal disease, a urological or sexual disorder, cancer, and a genetic disorder.

In some embodiments, the treating comprises mediating NO production in the subject. In some embodiments, the mediating comprises inhibiting NO production. In some embodiments, administration of the compound provided herein, or a pharmaceutically acceptable salt thereof, results in about equivalent reduced NO production in the subject compared to administration of L-arginine to a subject at the same concentration (e.g., administration of 100 nM to a subject results in about equivalent NO production in the subject compared to administering about 100 nM L-arginine to the subject).

In some embodiments, the disease or disorder is a neurological disorder. In some embodiments, the treating comprises reducing brain oxidative stress in the subject, reducing neuroinflammation in the subject, reducing proapoptotic signaling in the subject, mediating NO production in the subject, or any combination thereof. In some embodiments, the psychiatric disorder is major depressive disorder (MDD) or an anxiety disorder. In some embodiments, the psychiatric disorder is major depressive disorder (MDD). In some embodiments, the psychiatric disorder is an anxiety disorder. In some embodiments, the mediating comprises inhibiting.

In some embodiments, the disease or disorder is a cardiovascular or renal disease. In some embodiments, the cardiovascular or renal disease comprises hypertension.

In some embodiments, the disease or disorder is postprandial endothelial dysfunction.

In some embodiments, the disease or disorder is a urological or sexual disorder. In some embodiments, the urological or sexual disorder is erectile dysfunction.

In some embodiments, the disease or disorder is a neurodegenerative disease. In some embodiments, the neurodegenerative disease is Alzheimer's disease.

In some embodiments, the disease or disorder is cancer. In some embodiments, treating a cancer comprises slowing tumor growth and inhibiting tumor metastases, improving immune function of cancer patients. In some embodiments, the cancer is selected from the group consisting of breast cancer, sarcoma, and lung cancer, etc.

In some embodiments, the disease or disorder is a genetic disorder. In some embodiments, the genetic disorder is Duchenne Muscular Dystrophy (DMD) or autism spectrum disorder. In some embodiments, the genetic disorder is Duchenne Muscular Dystrophy (DMD). In some embodiments, the genetic disorder is autism spectrum disorder.

In some embodiments, the method provided herein is a method of treating the disease or disorder in the subject. As used herein, the phrase "therapeutically effective amount" refers to the amount of active compound (e.g., 2-amino-5-guanidino-N-(4-guanidinobutyl)pentanamide) or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a subject is about 1 mg to about 10 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

In some embodiments, the method provided herein is a method of preventing the disease or disorder in the subject. As used herein, the term "preventing" refers to preventing a disease, condition, or disorder in an individual who may be predisposed to the disease, condition or disorder but does not yet experience or display the pathology or symptomatology of the disease.

In some embodiments, the method provided herein is an in vivo method. In some embodiments, the method provided herein is an in vitro method.

In some embodiments, the present application provides a method of monitoring NO production in a subject, comprising:

i) administering to the subject an effective amount of a compound provided herein, or a pharmaceutically acceptable salt thereof; and ii) measuring the NO concentrations in the subject.

In some embodiments, the method further comprises obtaining a first biological sample from the subject (e.g., a blood sample) before the administering of step i). In some embodiments, the method further comprises measuring the NO levels in the first biological sample. In some embodiments, the method further comprises obtaining a second biological sample from the subject after the administering of step i). In some embodiments, the measuring of step ii) is performed on the second biological sample obtained from the subject. In some embodiments, the method is performed one or more times over a period of time (e.g., over a period of 1 week, 4 weeks, 12 weeks, 24 weeks, 36 weeks, 48 weeks, 52 weeks, etc).

In some embodiments, the present application provides a method of monitoring L-arginine levels in a subject, comprising:

i) administering to the subject an effective amount of a compound provided herein, or a pharmaceutically acceptable salt thereof; and ii) measuring the L-arginine concentrations in the subject.

In some embodiments, the method further comprises obtaining a first biological sample from the subject (e.g., a blood sample) before the administering of step i). In some embodiments, the method further comprises measuring the L-arginine levels in the first biological sample. In some embodiments, the method further comprises obtaining a second biological sample from the subject after the administering of step i). In some embodiments, the measuring of step ii) is performed on the second biological sample obtained from the subject. In some embodiments, the method is performed one or more times over a period of time (e.g., over a period of 1 week, 4 weeks, 12 weeks, 24 weeks, 36 weeks, 48 weeks, 52 weeks, etc).

In some embodiments, the present application provides a method of monitoring agmatine levels in a subject, comprising:

i) administering to the subject an effective amount of a compound provided herein, or a pharmaceutically acceptable salt thereof; and ii) measuring the agmatine concentrations in the subject.

In some embodiments, the method further comprises obtaining a first biological sample from the subject (e.g., a blood sample) before the administering of step i). In some embodiments, the method further comprises measuring the agmatine levels in the first biological sample. In some embodiments, the method further comprises obtaining a second biological sample from the subject after the administering of step i). In some embodiments, the measuring of step ii) is performed on the second biological sample obtained from the subject. In some embodiments, the method is performed one or more times over a period of time (e.g., over a period of 1 week, 4 weeks, 12 weeks, 24 weeks, 36 weeks, 48 weeks, 52 weeks, etc).

Combination Therapies

One or more additional therapeutic agents (e.g., one, two, three, four, or more additional therapeutic agents) such as, for example, a therapeutic agent provided herein, can be used in combination with a compound provided herein, or a pharmaceutically acceptable salt thereof, for treatment of the diseases or disorders provided herein.

In some embodiments, the additional therapeutic agent is selected from an anti-inflammatory agent, chemotherapeutic agent, a steroid, a PDE5 inhibitor, an antidepressant agent, a selective serotonin reuptake inhibitor (SSRI), a serotonin-norepinephrine reuptake inhibitor (SNRI), and an anesthetic (e.g., for use in combination with a surgical procedure).

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example steroids include, but are not limited to, corticosteroids such as cortisone, dexamethasone, hydrocortisone, methylprednisolone, prednisolone, and prednisone.

Example PDE5 inhibitors include, but are not limited to, sildenafil (Viagra®), tadalafil (Cialis®), vardenafil (Levitra®), avanafil, lodenafil, mirodenafil, udenafil, and zaprinast.

Example antidepressant agents include, but are not limited to, tricyclic antidepressant agents, Desyrel (trazodone), Serzone (nefazodone), Wellbutrin (bupropion), Remeron (mirtazapine), Valdoxan (agomelatine), Stablon (tianeptine), Edronax (reboxetine), Bolvidon/Depnon, Norval/Tolvon (mianserin), Insidon (opipramol), Spravato (esketamine), and ketamine. Example tricyclic antidepressant agents include, but are not limited to, Adapin (doxepin), Anafranil (clomipramine), Asendin (amoxapine), Endep/Elavil (amitriptyline), Ludiomil (maprotiline), Norpramin (desipramine), Pamelor (nortriptyline), Sinequan (doxepin), Surmontil (trimipramine), Tofranil (imipramine), Vivactil (protriptyline), Azafen (pipofezine), and Agedal/Elronon (noxiptiline).

Example Selective Serotonin Reuptake Inhibitors (SSRIs) include, but are not limited to, Luvox (fluvoxamine), Paxil (paroxetine), Prozac (fluoxetine), Zoloft (sertraline), Celexa (citalopram), Lexapro (escitalopram), Viibryd (vilazodone), and Brintellix (vortioxetine).

Example Serotonin-Norepinephrine Reuptake Inhibitors (SNRIs) include, but are not limited to, Effexor (venlafaxine), Cymbalta (duloxetine), Pristiq (desvenlafaxine), Savella (milnacipran), Fetzima (levomilnacipran).

Example anesthetics include, but are not limited to, local anesthetics (e.g., lidocaine, procain, ropivacaine) and general anesthetics (e.g., desflurane, enflurane, halothane, isoflurane, methoxyflurane, nitrous oxide, sevoflurane, amobarbital, methohexital, thiamylal, thiopental, diazepam, lorazepam, midazolam, etomidate, ketamine, propofol, alfentanil, fentanyl, remifentanil, buprenorphine, butorphanol, hydromorphone levorphanol, meperidine, methadone, morphine, nalbuphine, oxymorphone, pentazocine).

Example chemotherapeutic agents include, but are not limited to, alkylating agents, antimetabolites, anti-tumor antibiotics, topoisomerase inhibitors, mitotic inhibitors, kinase inhibitors, and hormone receptor inhibitors.

In some embodiments, the compound provided herein, or a pharmaceutically acceptable salt thereof, is administered as an adjunctive therapy in combination with one or more additional therapeutic agents, compared to a normal subject. In some embodiments, the additional therapeutic agent is administered simultaneously with a compound or composition provided herein. In some embodiments, the additional therapeutic agent is administered after administration of the compound or composition provided herein. In some embodiments, the additional therapeutic agent is administered prior to administration of the compound or composition herein. In some embodiments, the compound or composition provided herein is administered during a surgical procedure. In some embodiments, the compound or composition provided herein is administered in combination with an additional therapeutic agent during a surgical procedure.

The additional therapeutic agents provided herein can be effective over a wide dosage range and are generally administered in an effective amount. It will be understood, however, that the amount of the therapeutic agent actually administered will usually be determined by a physician, according to the relevant circumstances, including the condition to be imaged, the chosen route of administration, the actual compound administered, the age, weight, and response of the individual subject, the severity of the subject's symptoms, and the like.

Pharmaceutical Formulations

When employed as pharmaceuticals, the compounds and compositions provided herein can be administered in the form of pharmaceutical formulations. These formulations can be prepared as described herein or elsewhere, and can be administered by a variety of routes, depending upon whether local or systemic treatment is desired and upon the area to be treated. In some embodiments, the administration is selected from the group consisting of pulmonary administration (e.g., by inhalation or insufflation of powders or aerosols, including by nebulizer, intratracheal administration, or intranasal administration), oral administration, or parenteral administration (e.g., intravenous, intraarterial, subcutaneous, intraperitoneal, intramuscular or injection or infusion, intracranial, intrathecal, intraventricular administration, and the like). In some embodiments, the administration is intravenous or nasal administration.

Parenteral administration can be in the form of a single bolus dose, or may be, for example, by a continuous perfusion pump. Conventional pharmaceutical carriers, aqueous, powder, or oily bases, thickeners and the like, may be necessary or desirable.

Also provided are pharmaceutical formulations which contain, as the active ingredient, a composition provided herein in combination with one or more pharmaceutically acceptable carriers (excipients). In making a pharmaceutical formulation provided herein, the nanoparticle composition may be, for example, mixed with an excipient or diluted by an excipient. When the excipient serves as a diluent, it can be a solid, semi-solid, or liquid material, which acts as a vehicle, carrier, or medium for the nanoparticle composition. Thus, the pharmaceutical formulations can be in the form of powders, lozenges, elixirs, suspensions, emulsions, solutions, syrups, aerosols (as a solid or in a liquid medium), sterile injectable solutions, sterile packaged powders, and the like.

EXAMPLES

The invention will be described in greater detail by way of specific examples. The following examples are offered for illustrative purposes, and are not intended to limit the invention in any manner. The following materials were used throughout the Examples.

TABLE A

General Materials

| Material | Brand | Product No |
|---|---|---|
| Human Brain Microvascular Endothelial Cells P25 Flask | Cell systems | ACBRI 376 P25 |
| EndoGRO-MV-VEGF Complete Culture Media Kit | Millipore | SCME003 |
| Collagen type1 RAT tail | Corning | 354236 |
| 0.05 Trypsin-EDTA (1×) | Gibco | 25200-056 |
| Nitric-Oxide Cell-Based HTS Assay | Biovision | K979-100 |
| PBS 7.4 pH (10×) | Gibco | 70011-044 |
| 96-well flat bottom plates | Falcon | 351172 |
| 50 mL Conical tube | Falcon | 352098 |
| 1.5 mL Microcentrifuge Tube | Fisherbrand | 05-408-129 |
| 20 mm Tissue Culture Dish | BD Falcon | 353003 |
| CellTox Green Cytotoxicity | Promega | G8742 |

Example 1. 2-amino-5-guanidino-N-(4-guanidinobutyl)pentanamide

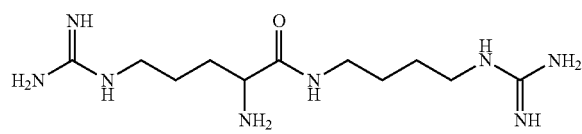 [SMILES: N=C(N)NCCCCNC(=O)C(N)CCCNC(=N)N]

Step 1. 5-(((benzyloxy)carbonyl)amino)-2-((tert-butoxycarbonyl)amino)pentanoic acid (Compound A)

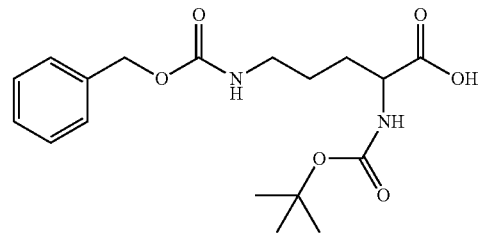 [SMILES: CC(C)(C)OC(=O)NC(CCCNC(=O)OCc1ccccc1)C(=O)O]

Sodium hydroxide (23.70 g, 0.59 mol) was added a saturated sodium bicarbonate solution (400 mL) and stirred for 15 minutes. N'-Cbz-L-Ornithine (31.56 g, 0.12 mol) was added and the mixture was stirred for half hour. Tetrahydrofuran (300 mL) and di-tert-butyl dicarbonate (28.46 g, 0.13 mol) were added. The mixture was stirred at room temperature overnight. Most of tetrahydrofuran was evaporated under reduced pressure. Ethyl acetate (200 mL) was mixed with residue. The PH of the aqueous layer was adjusted to 4 by adding hydrochloric acid solution (1.00 N). The ethyl acetate layer was separated, dried over magnesium sulfate and evaporated under reduced pressure. The residue was purified by column with hexane/acetone as solvent to give 43.40 g of the title compound. Molecular Formula: $C_{18}H_{26}N_2O_6$; Exact Mass: 366.18; MS (m/z): 366.76 (M+1)$^+$, 732.75 (2M+1)$^+$; HPLC RT: 15.54 min. (C8 reverse phase column: 250 mm; acetonitrile/water (0.05% trifluoroacetic acid); operation temperature: room temperature; detector: 210 nm).

Step 2. benzyl tert-butyl (5-((4-aminobutyl)amino)-5-oxopentane-1,4-diyl)dicarbamate (Compound B)

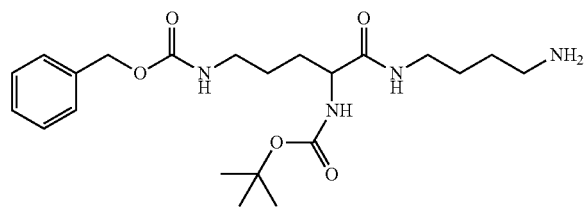 [SMILES: CC(C)(C)OC(=O)NC(CCCNC(=O)OCc1ccccc1)C(=O)NCCCCN]

5-(((benzyloxy)carbonyl)amino)-2-((tert-butoxycarbonyl)amino)pentanoic acid (43.40 g, 0.12 mol; Example 1, Step A) was dissolved in dichloromethane (600 mL). HBTU (67.25 g, 0.18 mol) and triethylamine (40 mL) were added. 1,4-Diaminobutane (31.34 g, 0.36 mol) was added slowly. The mixture was stirred at room temperature for a weekend. The mixture was filtered. The filtrate was washed with brine, dried over magnesium sulfate and evaporated under reduced pressure. The residue was purified by column with dichloromethane/methanol/triethylamine as solvent to give 16.36 g of the title compound. Molecular Formula: $C_{22}H_{36}N_4O_5$; Exact Mass: 436.27; MS (m/z): 437.21 $(M+1)^+$; HPLC RT: 13.31 min. (C8 reverse phase column: 250 mm; acetonitrile/water (0.05% trifluoroacetic acid); operation temperature: room temperature; detector: 210 nm).

Step 3. tert-butyl (5-amino-1-((4-aminobutyl)amino)-1-oxopentan-2-yl)carbamate (Compound C)

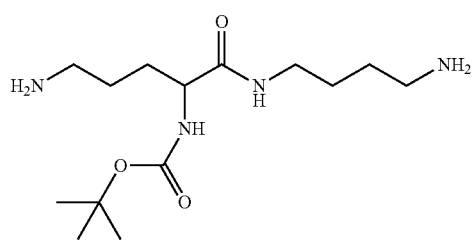 [SMILES: CC(C)(C)OC(=O)NC(CCCN)C(=O)NCCCCN]

Benzyl tert-butyl (5-((4-aminobutyl)amino)-5-oxopentane-1,4-diyl)dicarbamate (16.36 g, 37.50 mmol; Example 1, Step B) was dissolved in ethanol (200 mL). Two spatulas of Palladium (10% on activated carbon powder) were added. The mixture was stirred at room temperature under hydrogen atmosphere overnight. The mixture was filtered. The filtrate was evaporated under reduced pressure to give the crude product, which was used in the next step. Molecular Formula: $C_{14}H_{30}N_4O_3$; Exact Mass: 302.23; MS (m/z): 303.08 $(M+1)^+$; HPLC RT: 16.02 min. (C8 reverse phase column: 250 mm; acetonitrile/water (0.05% trifluoroacetic acid); operation temperature: room temperature; detector: 210 nm).

Step 4. Synthesis of Compound D

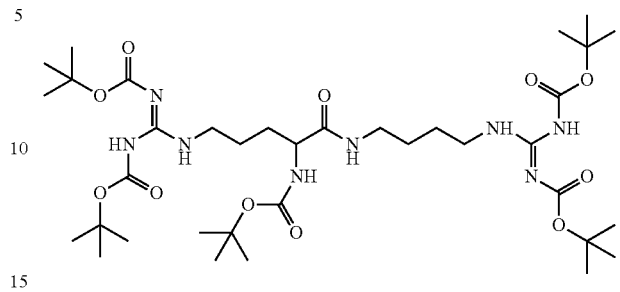

Crude tert-butyl (5-amino-1-((4-aminobutyl)amino)-1-oxopentan-2-yl)carbamate (Example 1, Step 3) was dissolved in tetrahydrofuran (120 mL). 1,3-Di-Boc-1H-pyrazole-1-carboxamidine (34.91 g, 0.11 mol), methanol (48 mL) and triethylamine (32 mL) were added. The mixture was stirred at room temperature under nitrogen atmosphere overnight and evaporated under reduced pressure. The residue was mixed with ethyl acetate (100 mL) and brine (100 mL). The ethyl acetate layer was separated, dried over magnesium sulfate and evaporated under reduced pressure. The residue was purified by column hexane/acetone as solvent as solvent to give 12.15 g of pure Compound D. Molecular Formula: $C_{36}H_{66}N_8O_{11}$; Exact Mass: 786.49; MS (m/z): 787.26 $(M+1)^+$; HPLC RT: 20.12 min. (C8 reverse phase column: 250 mm acetonitrile/water (0.05% trifluoroacetic acid); operation temperature: room temperature; detector: 210 nm).

Step 5. 2-amino-5-guanidino-N-(4-guanidinobutyl)pentanamide (Compound F)

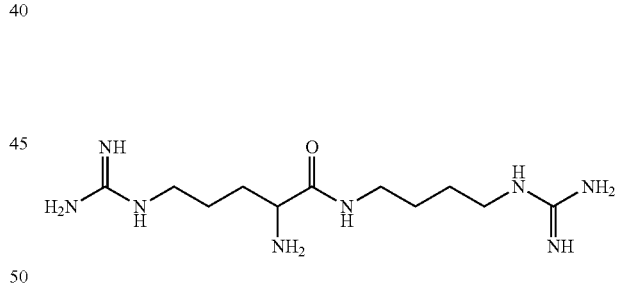

Compound D (Example 1, Step 4) was dissolved in dichloromethane (150 mL). Hydrogen chloride solution (4.0 N in dioxane, 75 mL) was added. The mixture was stirred at room temperature under nitrogen atmosphere overnight. The precipitate was collected, washed with dichloromethane and dried in vacuum to give 7.91 g of the title compound as the salt form. Molecular Formula: $C_{11}H_{26}N_8O$; Exact Mass: 286.22; MS (m/z): 287.27 $(M+1)^+$; HPLC RT: 3.86 min. (C8 reverse phase column: 250 mm; acetonitrile/water (0.05% trifluoroacetic acid); operation temperature: room temperature; detector: 210 nm). 1H NMR ($D_2O$), 1.55 (m, 6H), 1.80 (m. 2H), 3.33 (m. 6H), 3.88 (m, 1H).

Example 2. Cell Culture Preparation

Cell cultures were prepared using the following general procedures.

1. Under aseptic conditions 1×20 mm sterile tissue culture dish was coated with sterile 1:100 collagen for two hours at room temperature.
2. Under aseptic conditions 2× sterile 96 well-plates were coated with sterile 50 µL 1:100 collagen for two hours at room temperature.
3. After 2 hr collagen was recollected into 50 mL conical tube.
4. The petri dish and 2×96 well-plates were washed with warmed PBS.
5. Once 60% confluency of HBMVEC was observed, the plate was prepped for passage.
6. Media was aspirated from dish and washed with 1×PBS.
7. 1 mL of Trypsin was added, and the plate was transferred to 37° C. incubator for 1-2 min until cells appeared detached.
8. The plate was transferred back into sterile conditions and 2 mL of EndoGro Basal Media was added to inhibit Trypsin reaction.
9. Cells were pipetted 20× and thoroughly mixed before transferring into 25 mL of EndoGro Basal Media.
10. 100 µL of this mixture was added into each well both 96 well-plate.
11. Left over 5.8 mL of cell solution was transferred to petri dish previously coated with collagen and washed with 1×PBS.
12. Plates were incubated for 48 hours at 37° C.

Example 3. In Vitro Cell Cytotoxicity Assay Preparation

The following procedures were performed for the cell cytotoxicity assay (CellTox™ Green Cytotoxicity Assay; Promega Corporation). See also CellTox™ Green Cytotoxicity Assay, Instructions for Use of Products G8741, G8742, G8743, and G8731, revised May 2015, the disclosure of which is incorporated herein by reference in its entirety.

1. Samples containing 1:1000 L-Arginine (L-Arg; 100 nM, 10 µM, 100 µM, or 0.5 mL) or 1:1000 of 2-amino-5-guanidino-N-(4-guanidinobutyl)pentanamide (Example 1; 100 nM, 10 µM, 100 µM, or 0.5 mL) were prepared with EndoGro Basal Media without supplements (MWOS) into sterile 10×1 mL microcentrifuge tubes. For concentrations of 0, 1:1000 PBS to MWOS was made. Prepared samples are shown in Table 1.

2. Previously incubated cells were checked for confluency and transported into sterile biosafety cabinet.
3. Media from columns 2-6, rows B-G were aspirated and 100 µL of appropriate 2-amino-5-guanidino-N-(4-guanidinobutyl)pentanamide solutions were pipetted into each well before aspirating media from columns 7-11, rows B-G.
4. Once the wells were treated, plates were incubated at 37° C. for 24 hours and analyzed at 485-500 nm/520-530 nm after cytotoxicity assay treatment.

Figure 2:
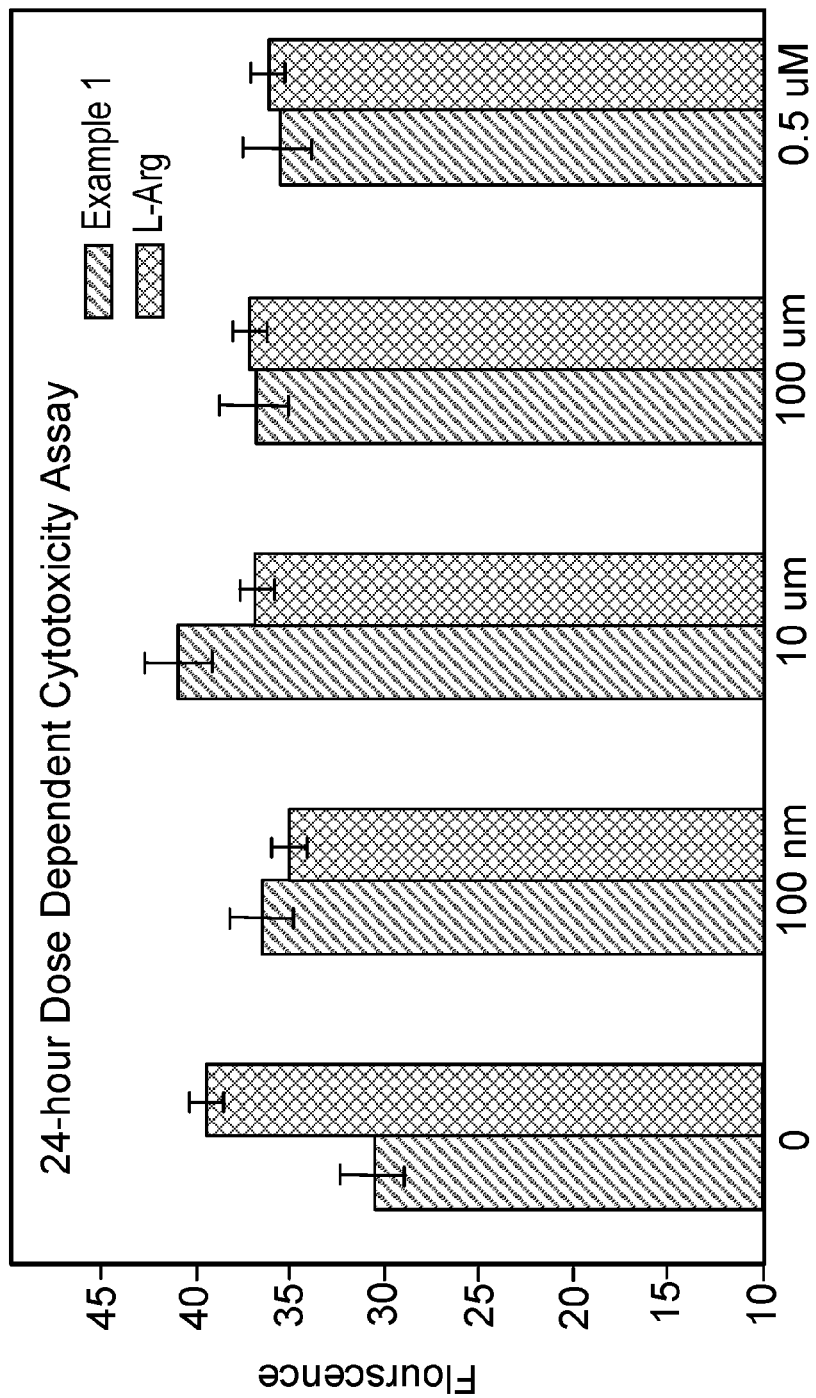
FIG. 2 shows results of a 24-hour dose dependent cytotoxicity assay comparing 2-amino-5-guanidino-N-(4-guanidinobutyl)pentanamide (Example 1) and L-arginine ("L-Arg").

Both L-arginine and 2-amino-5-guanidino-N-(4-guanidinobutyl)pentanamide were found to be non-toxic in the cellular model at the administered doses. As shown in FIG. 2, no significant difference in toxicity was observed for 2-amino-5-guanidino-N-(4-guanidinobutyl)pentanamide (Example 1) in comparison to L-arginine.

Example 4. In Vitro NO Detection Assay

The following general procedures were performed for the NO detection assay. See, e.g., Nitric Oxide Cell-Based HTS Assay Kit technical data sheet, Biovision Incorporated; Catalog #K979-10, September 2016, the disclosure of which is incorporated herein by reference in its entirety.

1. Performed cell culture protocol as described in Example 2.
2. Warmed all reagents in 37° C. water bath.
3. Master mix: 3 µL dye to 1.5 mL of Assay buffer for at least 60 wells.
4. Standard curve master mix: 5 µL NO stock solution to 95 µL NO Buffer for at least 60 wells.
5. Media was aspirated from column 1B-1G before aliquoting standard curve solution, as shown below in Table 2.

TABLE 2

| Sample | NO Buffer | NO Standard Curve Master Mix | Total |
|---|---|---|---|
| 1B | 50 µL | +0 µL | =50 µL |
| 1C | 48 µL | +2 µL | =50 µL |
| 1D | 46 µL | +4 µL | =50 µL |
| 1E | 44 µL | +6 µL | =50 µL |
| 1F | 42 µL | +8 µL | =50 µL |
| 1G | 40 µL | +10 µL | =50 µL |

6. Media was aspirated from 2B-2G through 6B-G before 50 µL aliquots of staining dye. This step was repeated for 7B-710 through 10B-10G.
7. Plates were incubated for 1 hour in 37° C.
8. After 1 hour, plates were transferred back into sterile conditions and washed 2× with EndoGro Media (previously warmed to 37° C.) before aliquoting the concentrations shown in Table 3 into each well.

TABLE 1

| | Example 1 | | | | | L-ARG | | | |
|---|---|---|---|---|---|---|---|---|---|
| | 2 | 3 (nM) | 4 (µM) | 5 (µM) | 6 (mM) | 7 | 8 (nM) | 9 (µM) | 10 (µM) | 11 (mM) |
| B | PBS | 100 | 10 | 100 | 0.5 | PBS | 100 | 10 | 100 | 0.5 |
| C | PBS | 100 | 10 | 100 | 0.5 | PBS | 100 | 10 | 100 | 0.5 |
| D | PBS | 100 | 10 | 100 | 0.5 | PBS | 100 | 10 | 100 | 0.5 |
| E | PBS | 100 | 10 | 100 | 0.5 | PBS | 100 | 10 | 100 | 0.5 |
| F | PBS | 100 | 10 | 100 | 0.5 | PBS | 100 | 10 | 100 | 0.5 |
| G | PBS | 100 | 10 | 100 | 0.5 | PBS | 100 | 10 | 100 | 0.5 |

TABLE 3

| | | Example 1 | | | | | L-ARG | | | |
|---|---|---|---|---|---|---|---|---|---|---|
| 1 | 2 | 3 (nM) | 4 (μM) | 5 (μM) | 6 (mM) | 7 | 8 (nM) | 9 (μM) | 10 (μM) | 11 (mM) |
| B | PBS | 100 | 10 | 100 | 0.5 | PBS | 100 | 10 | 100 | 0.5 |
| C | PBS | 100 | 10 | 100 | 0.5 | PBS | 100 | 10 | 100 | 0.5 |
| D | PBS | 100 | 10 | 100 | 0.5 | PBS | 100 | 10 | 100 | 0.5 |
| E | PBS | 100 | 10 | 100 | 0.5 | PBS | 100 | 10 | 100 | 0.5 |
| F | PBS | 100 | 10 | 100 | 0.5 | PBS | 100 | 10 | 100 | 0.5 |
| G | PBS | 100 | 10 | 100 | 0.5 | PBS | 100 | 10 | 100 | 0.5 |

9. Plates were incubated at 37° C. and analyzed every 15 mins for 1 h.

Figure 3:
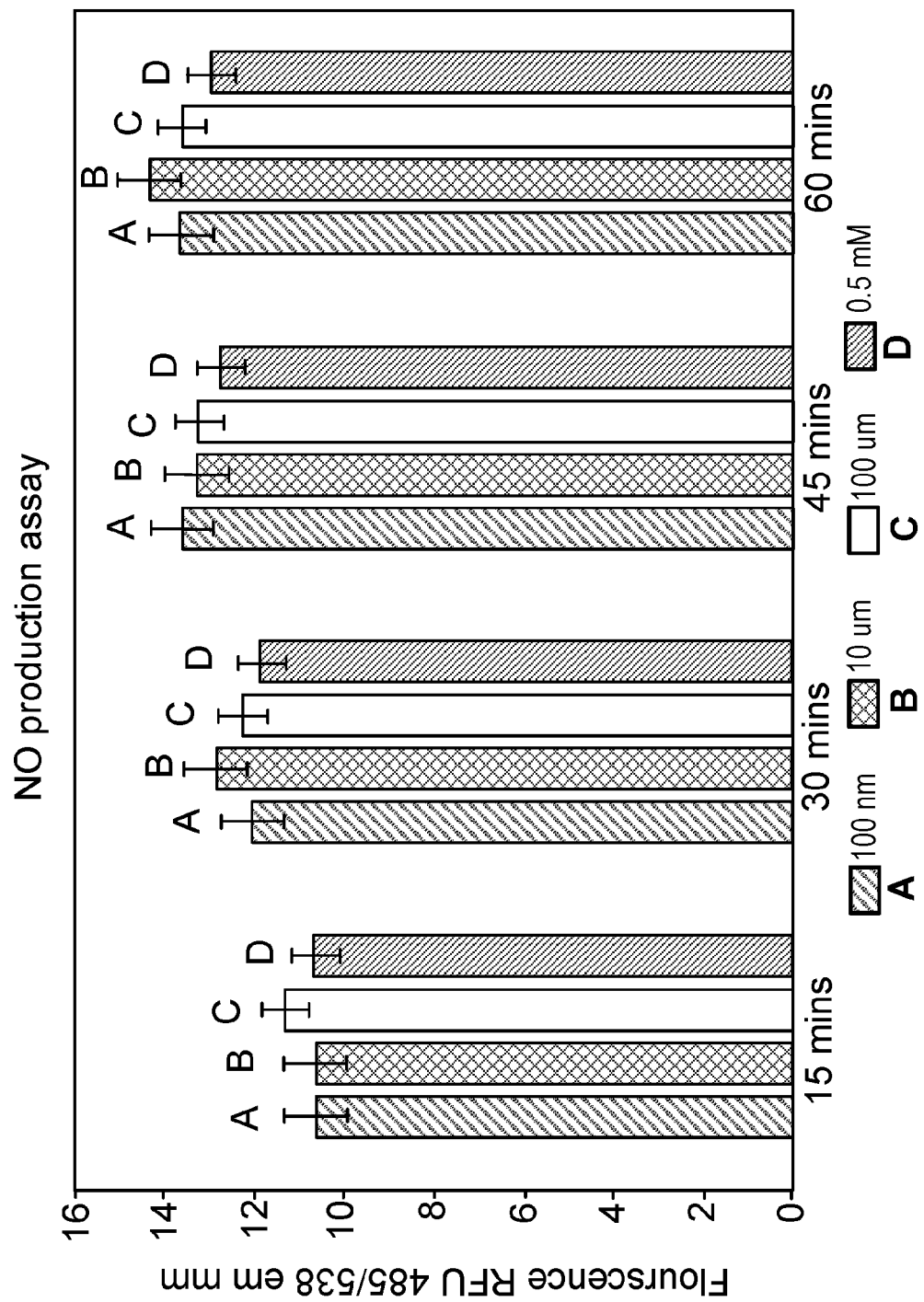
FIG. 3 shows results of a nitric oxide (NO) production assay using 2-amino-5-guanidino-N-(4-guanidinobutyl)pentanamide (Example 1). "A" Bars: 100 nm; "B" bars: 10 µM; "C" bars: 100 µM; "D" bars: 0.5 mM.
Figure 4:
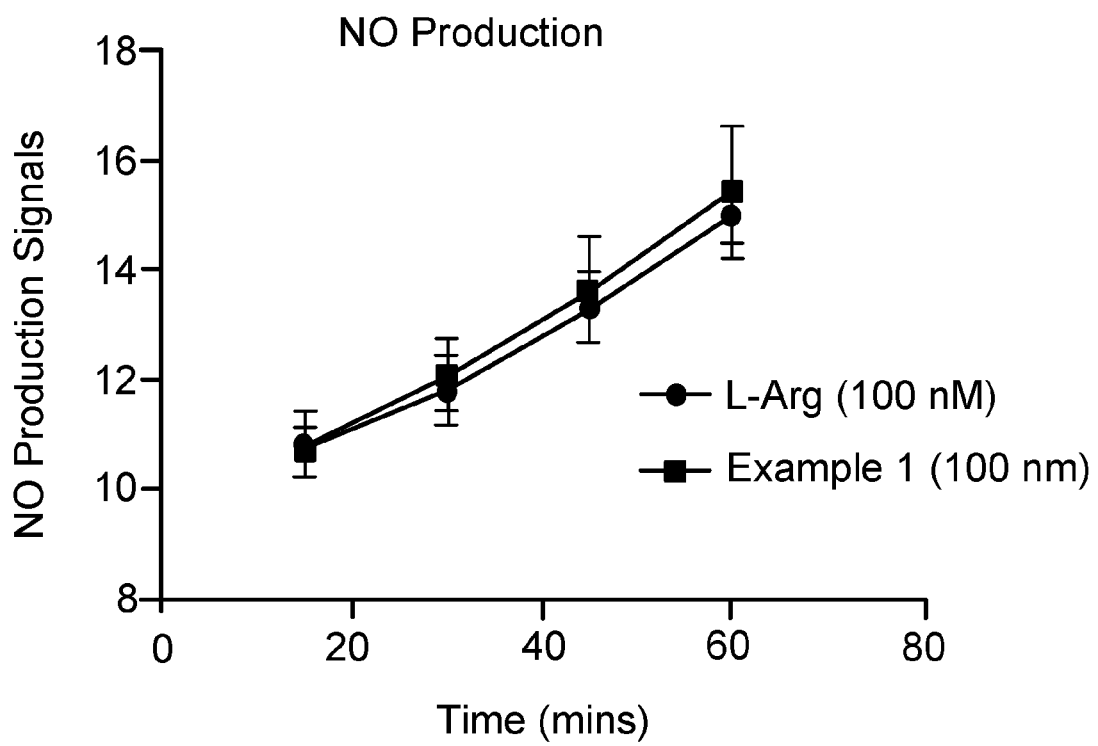
FIG. 4 shows a comparison of NO production signals observed in a cellular assay using L-arginine ("L-Arg") and 2-amino-5-guanidino-N-(4-guanidinobutyl)pentanamide (Example 1).

Results of the NO detection assay are shown in FIGS. 3-4. It was found that 2-amino-5-guanidino-N-(4-guanidinobutyl)pentanamide (Example 1) and L-arginine exhibited nearly identical capacity for mediating NO production (see FIGS. 3-4).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound, which is:

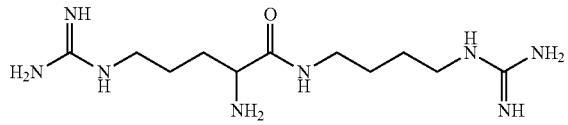 [SMILES: N=C(N)NCCCCNC(=O)C(N)CCCNC(=N)N]

or a pharmaceutically acceptable salt thereof.

2. The compound of claim 1, which is:

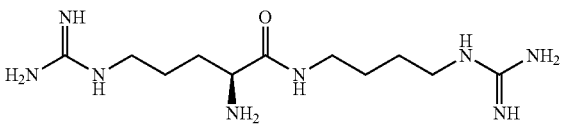 [SMILES: N=C(N)NCCCCNC(=O)[C@@H](N)CCCNC(=N)N]

or a pharmaceutically acceptable salt thereof.

3. A pharmaceutical composition comprising the compound of claim 1, or a pharmaceutically acceptable salt thereof, and a pharmaceutically acceptable carrier.

4. A method of increasing the global arginine bioavailability ratio (GABR) in a subject, comprising administering to the subject an effective amount of the compound of claim 1, or a pharmaceutically acceptable salt thereof.

5. A method of treating hypertension in a subject, the method comprising administering to the subject an effective amount of the compound of claim 1, or a pharmaceutically acceptable salt thereof.

6. The compound of claim 1, wherein the pharmaceutically acceptable salt is hydrochloride.

* * * * *